United States Patent [19]

Pike

[11] 4,104,296

[45] Aug. 1, 1978

[54] ORGANOFUNCTIONAL SILICON COMPOUNDS

[75] Inventor: Roscoe A. Pike, Simsbury, Conn.

[73] Assignee: Union Carbide Corporation, New York, N.Y.

[21] Appl. No.: 785,110

[22] Filed: Apr. 6, 1977

Related U.S. Application Data

[63] Continuation of Ser. No. 76,321, Sep. 28, 1970, abandoned.

[51] Int. Cl.² .............................. C07F 7/10; C07F 7/18
[52] U.S. Cl. ............................................. 260/448.8 R
[58] Field of Search .................. 260/448.2 N, 448.8 R

[56] References Cited

U.S. PATENT DOCUMENTS

| | | | |
|---|---|---|---|
| 2,919,173 | 12/1959 | Roff | 260/448.8 R X |
| 2,929,829 | 3/1960 | Morehouse | 260/448.2 N |
| 3,397,220 | 8/1968 | Klebe | 260/448.2 N |
| 3,440,261 | 4/1969 | Saam | 260/448.2 N |

*Primary Examiner*—Paul F. Shaver
*Attorney, Agent, or Firm*—Reynold J. Finnegan

[57] ABSTRACT

The invention relates to novel silicon compounds formed by the reaction of a lactone and an aminoalkyl silane or siloxane. These materials are useful to enhance adhesion of various resins to inorganic substrates.

7 Claims, No Drawings

ORGANOFUNCTIONAL SILICON COMPOUNDS

This application is a continuation of our prior U.S. application Ser. No. 76,321, filed on Sep. 28, 1970, now abandoned.

This invention relates to a new silicon-containing composition of matter, more particularly a silicon-containing composition of matter which contains an amide group and is the reaction product of a lactone with an aminoorgano silicon compound.

This invention is directed to silicon compounds having the average formula:

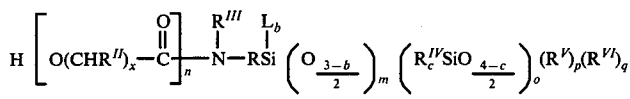

wherein $x$ is about 2 to about 8; $n$ is at least 1 and can be as large as 1000 or more; $b$ is 0, 1, or 2; $c$ is 0, 1, 2 or 3; $m$ is 0 or 1; $o$ is 0 or a positive number and $o$ is a positive number, $m$ is 1; $p$ is equal to 3-$b$ when $m$ is 0 and $o$ is 0, and when $m$ is 1, $p$ is 0; $q$ is 0 when $p$ is equal to 3-$b$ and $q$ is 0 or a positive number when $m$ is 1;

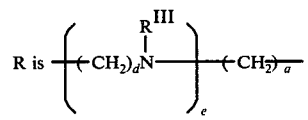

wherein $a$ is at least 3, typically not greater than 12, $d$ is at least 2 and typically not greater than 8, and $e$ is 0 or a positive number, preferably 0, 1 or 2; each $R^{II}$ is hydrogen and/or alkyl of 1 to about 4 carbon atoms; $R^{III}$ is hydrogen, alkyl, cycloalkyl, aryl, aminoalkyl, or hydroxyalkyl, which alkyls contain 1 to about 8 carbon atoms; L is a monovalent organic radical bonded to silicon by a carbon to silicon bond; $R^{IV}$ is silicon bonded and is hydrogen or an organic radical bonded to silicon by a carbon to silicon bond; $R^{V}$ is silicon bonded and is a hydrolyzable and condensable group such as hydroxyl, halide, alkali metaloxy, alkoxy, aroxy, acyloxy and the like; and $R^{VI}$ is bonded to oxygen and is hydrogen, alkyl, alkali metal, aryl, acyl and the like.

The silicon compounds of Formula I are obtained by the reaction of a lactone with a silicon compound having the average formula:

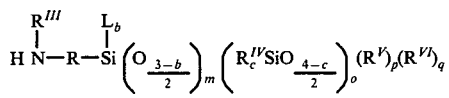

Illustrative of $R^{II}$ and $R^{III}$ (each limited by the description above) in the formula I above, other than hydrogen, where pertinent, are organic radicals such as alkyl, cycloalkyl, aryl, acyl, and the like, such as alkyl of 1-8 carbon (for example, methyl, ethyl, propyl, n-hexyl, and the like), aryl (such as phenyl, naphthyl, anthracyl and the like); cycloaliphatic (such as cyclohexyl, cyclooctyl and the like); acyl (such as formyl, acetyl, propionyl, butyryl, and the like); aminoalkyl (such as aminomethyl, gamma-aminopropyl, delta-aminobutyl, and the like); hydroxyalkyl (such as hydroxymethyl, gamma-hydroxypropyl, and the like).

In the case of L and $R^{IV}$, where both are organic radicals bonded to silicon by a carbon to silicon bond, illustrative radicals include those cited for $R^{II}$ and $R^{III}$ above, as well as other organic radicals such as halohydrocarbyls, urea substituted hydrocarbons, and essentially any other organic radical which does not significantly interfere with the reaction of lactone and the amino substituted silicon compound of Formula II to form a compound characterized by Formula I. With respect to the substituents present in the silicon compounds encompassed by Formula II, none should interfere with the reaction of the lactone with the amino substituent to form the compounds of Formula I. This represents the only real limitation in the nature of the amino substituted silicon compounds encompassed by Formula II. It is true that certain substituents as hydroxyalkyl might interfere or compete in the reaction with lactone, but the statistical result of such competitive reactions will result in an insolatable product which is encompassed by Formula I.

The amines which may be treated in accordance with the process of this invention are those which are described in U.S. Pat. No. 2,971,864, patented Feb. 14, 1961, specific embodiments being illustrated in examples 1, 2, 3, 4 and 6 thereof; U.S. Pat. No. 2,832,754, particularly at Examples 1, 2, 3 and 4 thereof; and U.S. Pat. No. 2,942,019 at columns 1, 2, 3 to line 17 of column 4 with respect to silanes and siloxane homopolymers and copolymers which are described therein to be reacted with aldehydes and ketones.

The lactones reacted with the silicon compound of Formula II to produce the product of Formula I are encompassed by the formula:

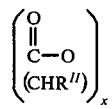

wherein each $R^{II}$ and $x$ are defined above. Illustrative of lactones covered by Formula III are beta-propiolactone; 2-butyrolactone; 2-valerolactone; epsilon-caprolactone, alkyl, alkoxy, cycloalkyl, aryl, and aralkyl substituted epsilon-caprolactone, and the like. Illustrative of the substituted lactones are the various monoalkyl epsilon-caprolactones, such as the monomethyl, monoethyl, monopropyl, monoisopropyl-, and the like, to monododecyl-epsilon-caprolactones; dialkyl epsilon-caprolactones in which the two alkyl groups are substituted on the same or different carbon atoms but not both on the epsilon carbon atom; trialkyl epsilon-caprolactones in which two or three carbon atoms in the lactone ring are substituted, so long as the epsilon carbon atom is not di-substituted; alkoxy-epsilon-caprolactones such as methoxy and ethoxy epsilon-caprolactones; and cycloalkyl, aryl, and the aralkyl epsilon-caprolactones such as cyclohexyl, phenyl and benzyl epsilon-caprolactones.

The process to produce the silicon compounds of Formula I involves reacting the appropriate silicon compound of Formula II with the desired lactone of Formula III. The reaction can occur at extremely low temperatures to higher temperatures depending upon the nature of the reactants. In the case of lactones having 5 ring carbon atoms or less, the reaction is favorably conducted in the presence of a solvent at moderate temperatures, viz., 100° C. and below. The reaction in the case of lactones containing more than 5 carbon atoms specifically 6 carbon atoms and greater, temperatures higher than 50° C. are normally employed since the reaction is not quite as fast and heat input is generally needed. Because the reaction of the lactone with the amino group of the silicon compound of Formula II is essentially quantitative in respect to the amino, the products can be isolated simply by removal of solvent employed or any excess lactone, preferably under reduced pressure. In the case of the reaction of the lactones containing less than 5 carbon atoms, it is desirable because of the apparent exothermic nature of the reaction to control the rate of reaction with solvent. The solvent acts as a heat transfer agent to help dissipate the heat generated by the reaction and to assist the course of the reaction to give the desired product. With some exceptions, when employing nitrile and ether solvents and $R^{III}$ is hydrogen, hydroxy alkylamido compounds are obtained. However, in the case of secondary amines, that is, when $R^{III}$ is other than hydrogen such as alkyl, the ether solvents are normally employed to enhance obtaining hydroxyalkylamido compounds. Illustrative solvents include, by way of example, dimethyl ether, diethyl ether, di-n-propyl ether, diisopropyl ether, tetrahydrofuran, dimethyl ether of ethylene glycol and the like; nitriles such as acetonitrile, propionitrile, butyronitrile, and the like; tertiary amides such as N,N-dimethyl formamide and N,N-dimethyl acetamide and the like; dialkyl sulfoxides such as dimethyl sulfoxide, diethyl sulfoxide, and the like.

In the case of the lower lactones, that is, 5 carbon atoms or less, the solvent is typically employed in an amount equal in volume to the amount of amine used, that is, an equal volume amount of solvent to the volume of the silicon compound of Formula II employed. However, this volume ratio can vary from about 0.1 to about 10 volumes of solvent for each volume of the aminosilicon compound of Formula II without undue effect on the course of reaction. Volume ratios of solvent to silicon compound of Formula II of about 0.5 to about 2 are preferred.

In the case of these lower lactones, it is oftentimes important to exert care in the manner of combining the reactants. The preferred method involves adding the lower lactone to a solvent solution of the aminosilicon compound of Formula II. In this way, one can easily control the temperature of the reaction.

In the case of the lower lactones, the reaction of silicon compound of Formula II with the lactone is typically exothermic, and therefore, to minimize the effect of heat of reaction, it is desirable to employ relatively low temperatures, viz., below about 40° C., typically in the range of about 0° C. to about 10° C. If the amino group is primary, then the reaction generally moves with great rapidity in the case of these lower lactones, but when the amine is secondary, the reaction is generally more sluggish, and therefore, it may be desirable in such cases to introduce heat to the reaction, typically to temperatures not in excess of the boiling point of the aminosilicon compound characterized by Formula II. In the case of the lower lactone, it is desirable not to run the reaction at temperatures greater than the boiling point of the solvent employed. However, in the case of the higher lactones, the reaction between the lactone and the aminosilicon compound of Formula II may be considerably higher, typically greater than about 40° C. and may range as high as 300° C. Generally, these higher lactones favorably react at temperatures in the range of about 100° C. to about 240° C.

In the case of these higher lactones, it is oftentimes desirable to employ a catalyst to induce the reaction. Useful catalysts for these purposes are tin catalysts, described in U.S. Pat. No. 2,890,208, patented June 9, 1959, other metal catalysts such as described at column 9 of U.S. Pat. No. 3,169,945, patented Feb. 16, 1965, the acid catalysts described at column 1, lines 37–40 of U.S. Pat. No. 2,914,556, patented Nov. 24, 1959, and the process described in U.S. Pat. 3,284,417.

The reaction of the lactone with the aminosilicon compound of Formula II may be effected with heat alone, though the higher molecular weight products containing polyester are more difficult to obtain by this procedure.

In most cases, the reaction of the lactone with the aminosilicon compound of Formula II is quantitative; consequently, equal mole amounts of the reactants can be employed to give complete conversion of the amino groups to hydroxy alkylamide or polyester amide. However, to insure complete reaction, it is generally preferred to carry out the reaction using an excess of lactone or a mole amount at least comparable to the value of $n$ defined in Formula I. Thus the ratio of lactone to the silicon compound of Formula II is dependent upon the desired molecular weight indicated by the value of $n$. If $n$ is to be 1, then an equal mole ratio or slight excess of lactone to aminosilicon compound may be employed, such as mole ratios of 1:1 to 3:1 with preferred ranges being 1:1 to 1.1:1. In the case of higher molecular weight polylactones (i.e., polyester) characterized by Formula I, the molecular ratio of lactone to aminosilicon compound of Formula I can be as high as 1000:1, preferably not greater than about 100:1.

The silicon compounds of this invention have a number of remarkable utilities. The high molecular weight lactone polyester silicon polymers where $n$ is 10, or greater, are readily compatible in a number of resins such as polyurethane resins, polyvinylchloride resins, phenolic resins and can be used as plasticizers therefor. If the silicon compound of Formula I is either hydrolyzable or condensable, then such product also improves the bond of the resins to a plurality of substrates such as glass (glass fiber and plate glass), metal, and the like. In addition, the compounds of Formula I, broadly speaking, have effectiveness as anti-foam agents in aqueous systems. The higher molecular weight silicon compounds of Formula I where $n$ is greater than 5 often exhibit interesting surfactant properties suggesting their use in foam manufacture. In addition, when $m$ is 1 of Formula I, the compounds exhibit good low temperature qualities suggesting their use as low temperature modifiers of a number of resins adversely affected by such low temperatures.

Though the examples below demonstrate specific embodiments of this invention, it is not intended that the invention be limited thereby.

EXAMPLE 1

Into a 500 milliliter three-necked flask fitted with stirrer, thermometer, and dropping funnel is charged 117.5 grams (0.5 mole) of N-methyl-gamma-aminopropyltriethoxysilane and 200 cc. of diethyl ether. The solution is cooled to 2° C. in an ice bath. Over an 0.75 hour period is added dropwise with stirring, 36 grams (0.5 mole) of beta-propiolactone at a rate to maintain the temperature of the reaction between 2° C. and 10° C. After the addition is complete the solution is allowed to warm to room temperature (about 25° C.). The product is obtained by concentrating the solution on a steam bath under a nitrogen sparge. There is obtained 140 grams of clear, light yellow liquid.

Analysis: Calculated for $C_{13}H_{29}SiNO_5$: Si, 9.12; N, 4.56; OEt, 44.0. Found: Si, 9.6; N, 4.6; OEt, 42.0.

The infrared spectrum of the adduct confirms the structure of the product to be

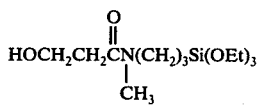

(N-methyl, N-beta-hydroxypropioyl-gamma-aminopropyltriethoxysilane).

EXAMPLE 2

In a 500 milliliter three-necked flask equipped with dropping funnel, stirrer and thermometer is charged 110.5 grams (0.5 mole) of gamma-aminopropyltriethoxysilane and 200 cc. of dry acetonitrile. The solution is cooled to 3° C. using an ice bath. Over the course of 0.75 hour, 36 grams (0.5 mole) of beta-propiolactone is added while maintaining the temperature of the reaction between 2° and 10° C. After the addition is complete the solution is warmed to room temperature over a period of 1.5 hours. The solution is concentrated under reduced pressure (5 milliliters) while heating to 40° C. There is obtained 142.5 grams of clear colorless liquid, $n_D^{25} = 1.4564$.

Analysis: Calculated for $C_{12}H_{27}SiNO_5$: Si, 9.56; N, 4.77; OEt, 46.1 Found: Si, 9.4; N, 5.5; OEt, 41.9

Infrared spectrum shows presence of COH, NH, C=O, SiOEt groups. Also indicated is some cyclic compound. Material identified as

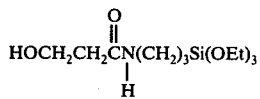

(N-beta-hydroxypropioyl-gamma-aminopropyltriethoxysilane) containing a small amount of

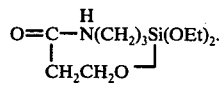

The compound is soluble in water, ethanol and acetone. Initially soluble in 95 per cent ethanol but on standing deposits a white solid characterized

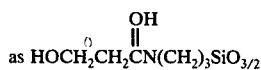

or polymer containing residual Si—OH groups.

A 10 per cent water solution of the above material is used to treat glass cloth followed by dyeing with an acid metallized dye. Fair coloration of the cloth is obtained using the hydroxy amido silicone.

95 Per cent ethanol-water solutions of the silane monomers of examples 1 and 2 are used to treat copper panels which are then heated to 235° C. for 50 hours to determine their effectiveness as metal protectants. The hydroxyamide materials are similar in effectiveness to the hydrolyzate of $NH_2CH_2CH_2NH(CH_2)_3Si(OEt)_3$ in protecting copper.

EXAMPLE 3

In a 250 cc. Erlenmeyer flask is charged 100 grams of a 4.8 weight per cent $[NH_2(CH_2)_4SiMeO]$ modified dimethylsilicone oil (i.e. $(CH_3)_2SiO$) (5000 molecular weight) and 50 cc. of diethyl ether. The solution is cooled to 0° C. in an ice bath and 2.16 grams beta-propiolactone is added. No noticeable reaction occurs. The solution is allowed to stand at room temperature 16 hours and is then concentrated under reduced pressure to give 177 grams of a clear colorless fluid. Viscosity of starting oil is 84.0 centipoises. The product has a viscosity of 2280 centipoises. The infrared spectrum has bands showing presence of C=O, COH, N—H, $Me_2SiO$. The product is a dimethylsilicone fluid modified with

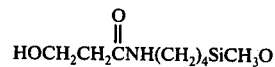

units.

EXAMPLE 4

In a 250 cc. Erlenmeyer flask is charged 100 grams of a 25 weight per cent $[NH_2(CH_2)_4SiMeO]$ dimethyl siloxane fluid of 1000 centistokes viscosity in 50 cc. of diethyl ether. The solution is cooled to 0° C. in an ice bath and 13.68 grams beta-propiolactone are added in two portions. Sufficient heat is evolved during the reaction to boil the ether solvent. The solution is allowed to stand 1 hour at room temperature then concentrated under reduced pressure (1 millimeter), while heating to 35° C. There is obtained 109 grams of a light yellow, extremely viscous, sticky fluid which flows very slowly.

EXAMPLE 5

Standard antifoam tests are conducted using an 0.5 per cent aqueous sodium oleate solution at an air flow of 1650 cubic centimeters per minute. The silicone fluid product of example 3 at 400 parts per million concentration allows a 500 cc. volume of foam to form in 30 seconds and in 3 minutes 1200 cc. of foam. At 800 parts per million concentration of the silicone fluid in 30 seconds, 350 cc. of foam is formed and in 3 minutes 1000 cc. of foam is formed and in 3 minutes 1000 cc. of foam is formed. Without the silicon fluid added, foam goes out of the test apparatus in 30 seconds.

EXAMPLE 6

The epoxy resin, diglycidyl ether of bisphenol A [2,2-bis(4-hydroxyphenyl)propane] is warmed to lower its viscosity and the silane to be evaluated is dissolved in the resin. The hardener, meta-phenylene diamine, is melted and stirred into the warm resin, 15 parts of hardener to 100 parts of resin are used. A wet layup is constructed of 12 plies of 181-112 glass cloth and warm resin. Polyethyleneterphthalate or cellophane sheeting is placed on both sides of the wet layup to serve as release agents. The wet layup is placed in a press and preheated to 250° C. Contact pressure is maintained for 9 minutes and the laminate is then cured for 21 minutes at 250° F. under 200 pounds per square inch pressure. After removing from the press the laminate is postcured for one hour at 400° F. Flexural strengths are determined on dry specimens and after exposure to boiling water for 72 hours.

Silanes as Integral Blends In Epoxy Resins

| Silane Additive | Wt-% Additive[a] | Flexural Strength psi Dry | 72 Hour Boil |
|---|---|---|---|
| None | — | 77,800 | 29,400 |
| HOCH$_2$CH$_2$$\overset{O}{\overset{\|}{C}}$N(CH$_2$)$_3$Si(OEt)$_3$ <br> $\phantom{HOCH_2CH_2}$H | 1 | 96,600 | 55,200 |
| HOCH$_2$CH$_2$$\overset{O}{\overset{\|}{C}}$N(CH$_3$)(CH$_2$)$_3$Si(OEt)$_3$ | 1 | 82,200 | 57,600 |

[a]Based on weight of resin.

EXAMPLE 7

The silane to be evaluated is dissolved in a phenolic resin (0.5 to 2.0 weight per cent silane based on resin solids). Strips of 181–112 glass cloth are passed through the resin solution, air dried and heated 2.5 to 3 minutes at 135° C. in an oven. Thirteen plies of the treated cloth are then placed in a press preheated to 290° F., contact pressure applied for 4 to 8 minutes and cure effected for 22 to 26 minutes at 290° F. at 200 pounds per square inch pressure. The press is cooled below 150° F. prior to removing the laminate. The laminate is then postcured as follows in a forced draft oven: 24 hours at 250° F., 24 hours at 300° F., 24 hours at 350° F. and 24 hours at 400° F. Flexural strengths are determined on the laminate as prepared and after aging 100 hours at 500° F.

Silanes as Integral Blends in Phenolic Resins

| Additive | Wt-%[a] Additive | Resin[b] Used | Flexural Strength, psi Initial | 100 hr. at 500° F. tested at 500° F. |
|---|---|---|---|---|
| None | — | V-204 | 34,700 | 11,000 |
| HOCH$_2$CH$_2$$\overset{O}{\overset{\|}{C}}$N(CH$_2$)$_3$Si(OEt)$_3$ <br> $\phantom{HOCH_2CH_2}$H | 1.5 | V-204 | 59,800 | 42,200 |
| HOCH$_2$CH$_2$$\overset{O}{\overset{\|}{C}}$N(CH$_3$)(CH$_2$)$_3$Si-(OEt)$_3$* | 1.5 | V-204 | 74,100 | 28,700 |

[a]Based on weight of resin.
[b]V-204 is a phenolic (phenol-formaldehyde resin manufactured by Plaskon Division of Allied Chemical Corporation

EXAMPLE 8

Employing the apparatus and procedure of Example 1, 0.5 mole of epsilon-caprolactone is charged to a mixture of 0.05 mole of gamma-aminopropyltriethoxysilane and 0.5 mole per cent stannous octoate, based on the weight of the reactants, followed by heating for 2 hours at 100° C. and then cooling. On concentrating the solution in a steam bath under vacuum there is obtainable product characterized by the formula:

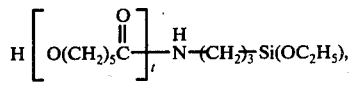

where $t$ ranges from 1 to about 20 and has an average of 10.

This silane is mixed in a 50:50 weight per cent solution of water and ethanol to produce a 3 weight per cent solution, based on silane content. A heat cleaned glass cloth is immersed in the solution and dried. When the cloth is coated with a polyvinyl chloride plastisol, in the usual manner, the bond of a plastisol to the cloth is superior to that obtained without silane treatment.

When the procedure of Example 8 is repeated but at 140° C., the average value of $t$ is 240. This product also provides enhanced bonding of polyvinyl chloride resins to glass cloth.

What is claimed is:

1. The silicon compounds having the average formula:

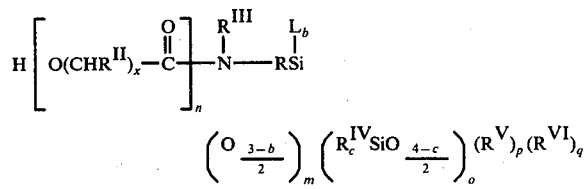

wherein $x$ is about 2 to 8; $n$ is at least 1; $b$ is 0, 1 or 2; $c$ is 0, 1, 2 or 3; $m$ is 0 or 1; $o$ is 0 or a positive number and when $o$ is a positive number, $m$ is 1; $p$ is equal to 3-$b$ when $m$ is 0 and $o$ is 0, and when $m$ is 1, $p$ is 0; $q$ is 0 when $p$ is equal to 3-$b$ and $q$ is 0 or a positive number when $m$ is 1;

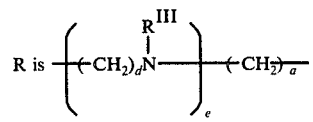

wherein (CH$_2$)$_d$ is bonded to Si; $a$ is at least 3; $d$ is at least 2; and $e$ is 0 or a positive number; each R$^{II}$ is hydrogen or alkyl of 1 to about 4 carbon atoms; R$^{III}$ is hydrogen, alkyl, cycloalkyl, aryl, aminoalkyl, or hydroxyalkyl, which alkyls contain 1 to about 8 carbon atoms; L is a monovalent organic radical bonded to silicon by a carbon to silicon bond; R$^{IV}$ is silicon bonded and is hydrogen or an organic radical bonded to silicon by a carbon to silicon bond; R$^{V}$ is silicon bonded and is one of a hydrolyzable or condensable group selected from the group consisting of hydroxyl, halide, alkali metaloxy, alkoxy, aroxy, and acyloxy; and R$^{VI}$ is bonded to oxygen and is hydrogen, alkyl, alkali metal, aryl, or acyl; provided that L and R$^{IV}$ are organic radicals which do not interfere with the reaction of the lactone and the amino substituent of the silicon compound as recited in claim 2.

2. The process of manufacturing the silicon compounds of claim 1 which comprises reacting a lactone with a silicon compound having the average formula:

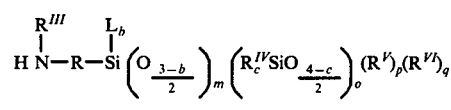

wherein R, $R^{III}$, $R^{IV}$, $R^{V}$, $R^{VI}$, L, b, c, m, o, p and q have the definitions recited for each as set forth in claim 1.

3. N-methyl, N-beta-hydroxypropioyl-gamma-amino-propyltriethoxysilane.

4. N-beta-hydroxypropioyl-gamma-aminopropyl-triethoxysilane.

5. A dimethylsilicone oil containing units therein having the structure

6. The silicon compound having the formula:

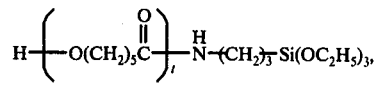

where t ranges from 1 to about 20.

7. The process of claim 2 wherein the lactone has the formula:

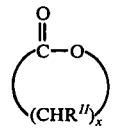

wherein $R^{II}$ is hydrogen or alkyl of 1 to about 4 carbon atoms and wherein x is about 2 to 8.

* * * * *